United States Patent [19]

Stölzer et al.

[11] 4,036,956
[45] July 19, 1977

[54] O,S,N-TRI-ALIPHATIC HYDROCARBON-THIONOTHIOLPHOSPHORIC ACID ESTER AMIDES AND PESTICIDAL COMPOSITION AND METHOD

[75] Inventors: Claus Stölzer, Wuppertal-Vohwinkel; Bernhard Homeyer, Opladen; Ingeborg Hammann, Cologne; Günter Unterstenhöfer, Opladen, all of Germany

[73] Assignee: Bayer Aktiengesellschaft, Leverkusen, Germany

[21] Appl. No.: 545,658

[22] Filed: Jan. 30, 1975

Related U.S. Application Data

[62] Division of Ser. No. 414,601, Nov. 8, 1973, Pat. No. 3,903,209, which is a division of Ser. No. 160,185, July 6, 1971, Pat. No. 3,793,407.

[30] Foreign Application Priority Data

July 11, 1970 Germany .......................... 2034475

[51] Int. Cl.² ........................ A01N 9/36; C07F 9/22
[52] U.S. Cl. ................................. 424/210; 260/940; 260/948; 260/949; 260/950; 260/956; 260/957; 424/216; 424/217; 424/219
[58] Field of Search .............. 260/940, 948, 949, 950, 260/956, 957; 424/210, 216, 217, 219

[56] References Cited

U.S. PATENT DOCUMENTS

| 2,971,020 | 2/1961 | Schrader ................ 260/940 |
| 3,072,702 | 1/1963 | Senkbeil ............... 260/959 X |
| 3,309,266 | 3/1967 | Magee .................. 260/959 X |
| 3,399,213 | 8/1968 | Osborne ................ 260/959 X |
| 3,454,682 | 7/1969 | Haynes et al. ........ 260/956 |
| 3,787,539 | 1/1974 | Colln et al. ........... 260/959 |

*Primary Examiner*—Richard L. Raymond
*Attorney, Agent, or Firm*—Burgess, Dinklage & Sprung

[57] ABSTRACT

O,S,N-tri-aliphatic hydrocarbon-thionothiolphosphoric acid ester amides of the general formula

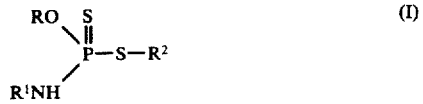

in which
R, R¹ and R², which may be the same or different, each is an alkyl, alkenyl or alkynyl radical with up to 6 carbon atoms, optionally substituted with at least one halo, phenyl, cyano, alkoxy, alkylmercapto, phenylmercapto or naphthylmercapto radical, the mercapto radicals being optionally chloro- or cyano-substituted, which possess nematocidal, insecticidal, acaridical, fungicidal and mammalian-repellent properties.

15 Claims, No Drawings

O,S,N-TRI-ALIPHATIC HYDROCARBON-THIONOTHIOLPHOSPHORIC ACID ESTER AMIDES AND PESTICIDAL COMPOSITION AND METHOD

This is a division of application Ser. No. 414,601, filed Nov. 8, 1973, now U.S. Pat. No. 3,903,209, issued Sept. 2, 1975, which is a division of application Ser. No. 160,185, filed July 6, 1971, now U.S. Pat. No. 3,793,407, issued Feb. 19, 1974.

The present invention relates to and has for its objects the provision of particular new O,S,N-tri-aliphatic hydrocarbon-thionothiolphosphoric acid ester amides, i.e. O,S, and N-(mono)-alkyl, alkenyl or alkynyl-thionothiolphosphoric acid ester amides, which posses nematocidal, insecticidal, acaricidal, fungicidal and mammalian-repellent properties, active compositions in the form of mixtures of such compounds with solid and liquid dispersible carrier vehicles, and methods for producing such compounds and for using such compounds in a new way especially for combating pests, e.g. nematodes, insects, acarids, fungi and destructive mammals, especially nematodes, insects and acarids, with other and further objects becoming apparent from a study of the within specification and accompanying examples.

It is known from German Published Specification No. 1,032,247 and German Patent Specifications Nos. 830,509 and 917,668 that certain O,O,S-trialkyl-thionophosphoric acid esters, for example the O,O-diethyl-S-2-ethylmercaptoethyl ester of thionothiolphosphoric acid (Compound A), possess insecticidal and acaricidal properties.

The present invention provides, as new compounds, the O-alkyl (alkenyl, alkynyl)-S-alkyl(alkenyl,alkynyl)-N-monoalkyl(alkenyl,alkynyl)thionothiolphosphoric acid ester amides of the general formula

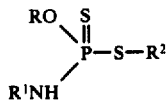

in which
R, R$^1$ and R$^2$, which may be the same or different, each is an alkyl, alkenyl or alkynyl radical with up to 6 carbon atoms, optionally substituted with at least one halo, phenyl, cyano, alkoxy, alkylmercapto, phenylmercapto or naphthylmercapto radical, the mercapto radicals being optionally chloro- or cyano-substituted.

The compounds of the formula (I) have been found to exhibit good insecticidal and acaricidal activity and a particularly strong nematocidal activity, as well as also exhibiting fungicidal activity and a repellent action towards destructive mammals.

The present invention also provides a process for the preparation of a compound of the formula (I), in which an O-alkyl(alkenyl,alkynyl)-N-monoalkyl(alkenyl,alkynyl) amido-thionothiolphosphoric acid ester salt of the general formula

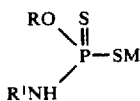

in which
R and R$^1$ have the meanings stated above, and
M stands for an alkali metal equivalent, an alkaline earth metal equivalent or an optionally alkyl-substituted ammonium equivalent,
is reacted with a compound of the general formula $$\text{Hal—R}^2 \qquad (III)$$

in which
R$^2$ has the meaning stated above, and
Hal stands for a halogen atom, preferably a chlorine or bromine atom.

Surprisingly, the novel thionothiolphosphoric acid ester amides of the general formula (I) possess not only very good insecticidal and acaricidal properties, but also a considerably higher nematocidal activity than the known O,O,S-trialkyl-phosphoric acid esters which are chemically the most closely comparable compounds of the same type of activity. The compounds of the invention are therefore an enrichment of the art.

If the potassium salt of O-ethyl-N-monoisopropylthionothiolphosphoric acid ester amide and 1-chloro-2-ethyl-mercaptoethane are used as starting materials, the reaction may be represented by the following equation:

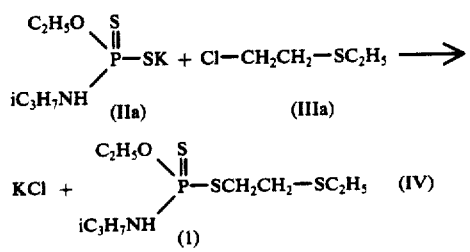

Preferably, R and R$^1$ each stands for a straight or branched-chain alkyl radical with 1–4 carbon atoms or an alkenyl radical with 2–4 carbon atoms, for example for methyl, ethyl n- or isopropyl, n-, iso-, sec.-or tert.-butyl or allyl. R$^2$ stands preferably for a straight-chain or branched alkyl radical with 1–4 carbon atoms or for allyl, methallyl or propargyl. Further preferred meanings for R, R$^1$ and R$^2$ — especially R$^2$ — are straight or branched-chain alkyl groups with 1–4 carbon atoms and alkenyl groups with 2–4 carbon atoms, which alkyl and alkenyl groups each carry at least one substituent selected from the group consisting of chlorine and bromine atoms and cyano, lower alkoxy, lower alkylmercapto, phenylmercapto and naphthylmercapto radicals, the said mercapto radicals being optionally chloro- or cyano-substituted. The preferred cyclic alkyl radical is cyclohexyl.

As examples of the starting materials of the formula (II), there may be mentioned the potassium, sodium and ammonium salts of O-methyl-N-methyl, O-methyl-N-ethyl, O-methyl-N-isopropyl, O-methyl-N-n-propyl, O-methyl-N-(n-, iso-, sec.- or tert.-)butyl-, O-ethyl-N-methyl-, O-ethyl-N-ethyl-, O-ethyl-N-n-propyl-, O-ethyl-N-isopropyl-, O-ethyl-N-(n-, iso-, sec.- or tert.)butyl-, O-n-propyl-N-methyl-, O-n-propyl-N-ethyl-, O-n-propyl-N-n-propyl-, O-n-propyl-N-isopropyl, O-n-propyl-N-(n-, iso-, sec.- or tert.-)butyl-, O-isopropyl-N-methyl-, O-isopropyl-N-ethyl-, O-iso-propyl-N-n-propyl-, O-isopropyl-N-isopropyl-, O-isopropyl-N-(n-, iso-, sec.- or tert.-) butyl-, O-(n-, iso-, sec.- or tert.-)buty-N-methyl-, O-(n-, iso-, sec. -or tert.-)butyl-N-ethyl and O-(n-, iso-, sec.- or tert.-)butyl-N-isopropyl-thionothiolphosphoric acid ester amides.

The preparative process is preferably carried out with the use of a solvent or diluent, for which purpose practically all inert organic solvents and diluents are suitable, especially aliphatic and aromatic optionally possibly chlorinated hydrocarbons, such as benzene, toluene, xylenes, benzine, methylene chloride, chloroform, carbon tetrachloride and chlorobenzene; ethers, such as diethyl ether, dibutyl ether and dioxane; ketones, such as acetone and methylethyl, methylisopropyl and methylisobutyl ketones; nitriles, such as acetonitrile; and alcohols, such as methanol, ethanol and propanol. In some cases also water may be used as solvent or diluent. The reaction temperatures can be varied within a fairly wide range; in general, the reaction is effected at about 0° to 100° C, preferably about 30° to 40° C.

The reaction is, in general, carried out at normal pressure.

When carrying out the process of the invention, the salts of the formula (II) and the halogen compounds of the formula (III) are, in most cases, used in equimolar amounts. An excess of one or the other of the reactants brings no substantial advantages. Preferably, the reaction is effected in one of the above-mentioned solvents at about 30° to 40° C; the reaction mixture is thereafter stirred for some hours and worked up according to any customary method.

The substances according to the invention are obtained in most cases in the form of colorless to slightly yellow-colored, viscous, water-insoluble oils which in many cases cannot be distilled without decomposition but which can, by so-called "slight distillation," that is by longer heating to moderately elevated temperatures under reduced pressure, be freed from the last volatile components and in this way be purified. For their characterization, the refractive index is especially suitable. Solid compounds are characterized by their melting points. As already mentioned, the compounds according to the invention are characterized by outstanding nematocidal, insecticidal and acaricidal properties. They possess at the same time a good effectiveness against both sucking and biting insects, Diptera, mites, as well as a systemic activity. In addition, they also show a fungitoxic effectiveness against phytopathogenic fungi, for example *Piricularia oryzae*, as well as a repellent action towards destructive mammals. The products, therefore, may be used with success in crop protection and the protection of stored products, as well as in the hygiene field, against the most diverse animal pests.

To the sucking insects contemplated herein there belong, in the main, aphids (Aphidae) such as the green peach aphid (*Myzus persicae*), the beam aphid (*Doralis fabae*), the bird cherry aphid (*Rhopalosiphum padi*), the pea aphid (*Macrosiphum pisi*) and the potato aphid (*Macrosiphum solanifolii*), *the rosy apple aphid (Sappaphis mali)*, the mealy plum aphid (*Hyalopterus arundinis*), the currant gall aphid (*Cryptomyzus korschelti*), and the cherry black-fly (*My is cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs for example the beet bug (*Piesma quadrata), the red cotton bug (Dysdercus intermedius*), the bed bug (*Cimex lectularius*), the assassin bug (*Rhodnius prolizus*) and Chagas' bug (*Triatoma infestans*) and, further, cicadas, such as Euscelis bilobatus and *Nephotettix bipunctatus;* and the like.

In the case of the biting insects contemplated herein, above all there should be mentioned butterfly caterpillars (Lepidoptera) such as the daimond-back moth (*Plutella maculipennis*), the gypsy moth (*Lymantria dispar*), the brown-tailed moth (*Euproctis chrysorrhoea*) and tent caterpillar (*Malacosoma neustria*); further, the cabbage moth (*Mammestra brassicae*) and the cutworm (Agrotis segetum), the large white butterfly (*Pleris brassicae*), the small winter moth (*Cheimatobia brumata*), the green oak tortrix moth (*Toutrix viridana*), the fall armyworm (*Laphygma frugiperda*) and cotton worm (*Prodenia litura*), the ermine moth (*Hyponomeuta padella*), the mediterranean flour moth (*Ephestia kuhniella*) and greater wax moth (Galleria mellonella); and the like.

Also to be classed with the biting insects contemplated herein are beetles (Coleoptera), for example the granary weevil (*Sitophilus granarius = Calandra granaria*) the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra or Sitophilus zeamais), the drugstore beetle (Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (Leucophaea or (*Rhyparobia maderae*), oriental cockroach (*Blatta orientalis*), the giant cockroach (*Blaberus giganteus*) and the black giant cockroach (*Blaberus fuscus*) as well as Henschoutedenia flexivitta; further, Orthoptera, for example the house cricket (*Acheta domesticus*); termites such as the eastern subterranean termite (*Reticulitermes flavipes*) and Hymenoptera such as ants, for example the garden ant (*Lasius niger*); and the like.

The Diptera contemplated herein comprise essentially the flies, such as the vinegar fly (*Drosophila melanogaster*), the Mediterranean fruit fly (Ceratitis capitata), the house fly (*Musca domestica*), the little house fly (Fannia canicularis), the black blow fly (*Phormia regina*) and bluebottle fly (*Calliphora erythrocephala*) as well as the stable fly (Stomoxys calcitrans); further, gnats, for example mosquitoes such as the yellwo fever mosquito (*Aedes aegypti*), the northern house mosquito (*Culex pipiens*) and the malaria mosquito (*Anopheles stephensi*); and the like.

With the mites (Acarina) contemplated herein there are classed, in particular, the spider mites (*Tetranychidae*) such as the two-spotted spider mite (*Tetranychus telarius = Tetranychus althaeae or Tetranychus urticae*) and the European red mite (*Paratetranychus pilosus = Panonychus ulmi*), gall mite, for example the black currant gall mite (*Eriophyes ribis*) and tarsonemides, for example the broad mite (*Hemitarsonemus latus*) and the cyclamen mite (*Tarsonemus pallidus*); finally, ticks, such as the relapsing fever tick (*Ornithodorus moubata*); and the like.

When applied against pests harmful to health and pests of stored products, especially flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usuable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, whereby, for example, in the case where water is used as diluent, organic solvents may be added as auxiliary solvents. The following may be cheifly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), sulfoxides (e.g. dimethyl sulfoxide, etc.), ketones (e.g. acetone, etc.), and/or water; as well as inert dispersible finely divided solid carrier, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixture with one another and/or with such solid and/or liquid dispersible carrier vehicles and/or with other known compatible active agents, especially plant protection agents, such as other acaricides, insecticides, fungicides, bactericides and nematocides, or rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus the present invention contemplates over-all compositions which composite mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, and an amount of the active compound which is effective for the purpose in question and which is generally between about 0.0001-95%, and preferably 0.01-95%, by weight of the mixture.

The active compounds can also be used in accordance with the well known ultra-low volume process with good success, i.e. by applying such compounds if normally a liquid, or by applying a liqud composition containing the same, via very effective atomizing equipment, in finely divided form, e.g. average particle diameter of from 50-100 microns, or even less, i.e. in mist form, for example by airplane crop straying techniques. Only up to at most about a few liters/heaters are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. nematodes, insects, acaride, fungi and destructive mammals and more particularly methods of combating at lease one of nematodes, insects and acarids which comprises applying to at least one of correspondingly (a) such nematodes, (b) such insects, (c) such acarids, (d) such fungi ard (f) the corresponding habitat thereof or of destructive mammalian pests, i.e. the locus to be protected, a correspondingly combative or toxic amount, i.e. a nematocidally, insecticidally, acaricidally, fungicidally, or mammalian-repellent effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Myzus test (contact action)

Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier and the concentrate is diluted with water to the desired concentration.

Cabbage plants (Srassica oleracea) which have been heavily infested with aphids (Myzus persicae) are sprayed with the preparation of the active compound until dripping wet.

After the specified periods of time, the degree of destruction is determined as a percentage: 100% means that all the aphids are killed whereas 0% means that none of the aphids are killed.

The active compounds, the concentrations of the active compounds, the evaluation times and the results can be seen from the following Table 1:

EXAMPLE 2

Tetranychus test

Solvent: 3 parts by weight acetone
Emulsifer: 1 part by weight alkylarylpolyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (Phaseolus vulgaris), which have a height of approximately 10-30 cm., are sprayed with the preparation of the active compound until driping wet. These Table 1

| (Myzus test) | | |
|---|---|---|
| Active compounds | Concentration of active compound in % by weight | Degree of destruction in % after 1 day |
| 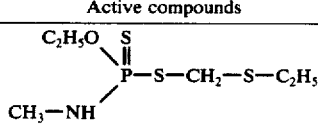 (2) | 0.1<br>0.01<br>0.001 | 100<br>100<br>98 |
| 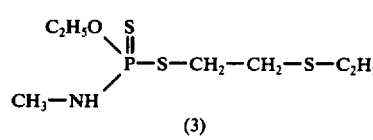 (3) | 0.1<br>0.01<br>0.001 | 100<br>98<br>40 |
| 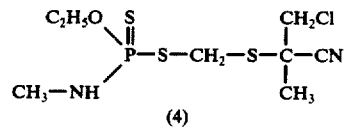 (4) | 0.1<br>0.01<br>0.001 | 100<br>100<br>99 |
| 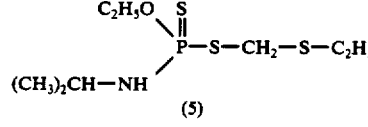 (5) | 0.1<br>0.01<br>0.001 | 100<br>99<br>65 |
| 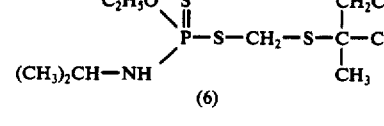 (6) | 0.1<br>0.01<br>0.001 | 100<br>98<br>95 |
| 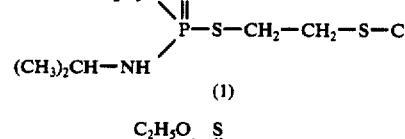 (1) | 0.1<br>0.01<br>0.001 | 100<br>99<br>95 |
| 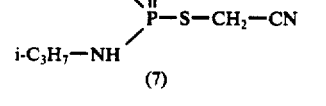 (7) | 0.1<br>0.01<br>0.001 | 100<br>99<br>75 |
| 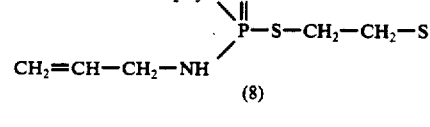 (8) | 0.1<br>0.01<br>0.001 | 100<br>100<br>50 |
| 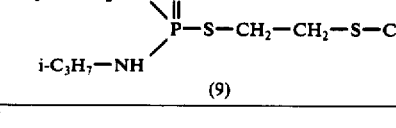 (9) | 0.1<br>0.01<br>0.001 | 100<br>100<br>75 | bean plants are heavily infested with spider mites (Tetranychus urtiene) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from the following Table 2:

with the stated amount of solvent, the stated amount of emulsifier is added and th concentrate is diluted with water to the desired concentration.

The preparation of active compound is intimately mixed with soil which is heavily infested with the test nematodes. The concentration of the active compound in the preparation is of practically no importance; only the amount of active compound per unit volume of soil, which is given in p.p.m., is decisive. The soil is filled into pots, lettuce is sown in and the pots are kept at a greenhouse temperature of 27° C. After 4 weeks, the Table 2

| (Tetranychus test) | | |
|---|---|---|
| Active compounds | Concentrations of active compound in % by weight | Degree of destruction in % after 2 days |
| $(C_2H_5O)_2\overset{\overset{S}{\|\|}}{P}-S-CH_2-CH_2-S-CH_2-CH_3$ (known) (A) | 0.1<br>0.01 | 95<br>0 |
| $\begin{array}{c}C_2H_5O\\ \phantom{xx}\diagdown\\ CH_3-NH\diagup\end{array}\overset{\overset{S}{\|\|}}{P}-S-CH_2-S-C_2H_5$ (2) | 0.1<br>0.01 | 100<br>100 |
| $\begin{array}{c}C_2H_5O\\ \phantom{xx}\diagdown\\ (CH_3)_2CH-NH\diagup\end{array}\overset{\overset{S}{\|\|}}{P}-S-CH_2-CH_2-Cl$ (10) | 0.1<br>0.01 | 99<br>98 |
| $\begin{array}{c}C_2H_5O\\ \phantom{xx}\diagdown\\ (CH_3)_2CH-NH\diagup\end{array}\overset{\overset{S}{\|\|}}{P}-S-CH_2-S-C_2H_5$ (5) | 0.1<br>0.01 | 100<br>90 |
| $\begin{array}{c}C_2H_5O\\ \phantom{xx}\diagdown\\ (CH_3)_2CH-NH\diagup\end{array}\overset{\overset{S}{\|\|}}{P}-S-CH_2-S-\underset{\underset{CH_3}{\|}}{\overset{\overset{CH_2Cl}{\|}}{C}}-CN$ (6) | 0.1<br>0.01 | 100<br>20 |
| $\begin{array}{c}C_2H_5O\\ \phantom{xx}\diagdown\\ (CH_3)_2CH-NH\diagup\end{array}\overset{\overset{S}{\|\|}}{P}-S-CH_2-CH_2-S-C_2H_5$ (1) | 0.1<br>0.01 | 100<br>100 |

EXAMPLE 3

Critical concentration test

Test nermatode: Meloidogyne sp.
Solvent: 3 parts by weight acetone
Emulsifier: 1 parts by weight alkylarylpolyglycol ether To produce a suitable preparation of active compound, 1 part by weight of active compound is mixed lettuce roots are examined for infestation with nematodes, and the degree of effectiveness of the active compound is determined as a percentage. The degree of effectiveness is 100% when the infestation is completely avoided; it is 0% when the infestation is exactly the same as in the case of the control plants in untreated soil which has been infested in the same manner.

The active compounds, the amounts applied and the results can be seen from the following Table 3:

Table 3

| (Hematocides Meloidogyne incognita) | | | | | | | |
|---|---|---|---|---|---|---|---|
| | Degree of destructon in % with a concentration of active compound in ppm of | | | | | | |
| Active compound | 50 | 40 | 20 | 10 | 5 | 2.5 | 1.25 |
| $\begin{array}{c}C_2H_5O\\ \phantom{xx}\diagdown\\ CH_3-NH\diagup\end{array}\overset{\overset{S}{\|\|}}{P}-S-CH_2-CH_2-S-C_2H_5$ (3) | 100 | 100 | 100 | 99 | 98 | 96 | |

Table 3-continued
(Hematocides Meloidogyne incognita)

| Active compound | Degree of destructon in % with a concentration of active compound in ppm of | | | | | | |
|---|---|---|---|---|---|---|---|
| | 50 | 40 | 20 | 10 | 5 | 2.5 | 1.25 |
| $C_2H_5O$–P(=S)(–NH–iC_3H_7)–S–CH_2–C≡CH  (11) | 100 | 99 | 99 | 95 | | | |
| $C_2H_5O$–P(=S)(–NH–iC_3H_7)–S–CH_2–S–C_2H_5  (5) | 100 | 100 | 100 | 100 | 95 | 0 | |
| $C_2H_5O$–P(=S)(–NH–iC_3H_7)–S–CH_2–CH_2–S–C_2H_5  (1) | 100 | 100 | 100 | 100 | 100 | 98 | 75 |
| $C_2H_5O$–P(=S)(–NH–CH_3)–S–CH_2–C≡CH  (12) | 100 | 100 | 98 | 93 | 0 | | |
| $C_2H_5O$–P(=S)(–NH–iC_3H_7)–S–CH_2–CH_2–Cl  (10) | 100 | 100 | 100 | 99 | 98 | 98 | 90 |
| $C_2H_5O$–P(=S)(–OC_2H_5)–S–CH_2–CH_2–SC_2H_5  (known) (A) | 98 | 90 | 0 | | | | |

The following example will illustrate the compounds of the invention.

EXAMPLE 4

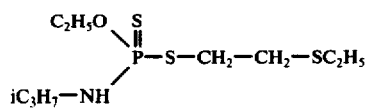

(1)

To 97.2 g (0.44 mole) of the sodium salt of O-ethyl-N-monoisopropylthionothiolphosphoric acid ester amide in 300 cc of acentonitrile there are added slowly, at 40°, 49.8 g (0.4 mole) of 1-chloro-2-ethyl mercapto-ethane. The mixture is afterwards stirred over-night at 40° C; it is poured into water; the mixture is taken up in benzene; the organic phase is washed neutral with water; it is dried over sodium sulfate; the drying agent is filtered off; the filtrate is concentrated and the residue obtained is distilled. 86.3 g (75.0% of theory) of O-ethyl-S-(2-ethyl-mercapto-ethyl)-N-monoisopropylthionothiolphosphoric acid ester amide are obtained as a yellow oil of boiling point 140° C/0.01 mm Hg and refractive index of $n_D^{21.5}$ of 1.5435.

Analogously, the following compounds are prepared:

| Constitution | Physical properties | |
|---|---|---|
| $C_2H_5O$–P(=S)(–NH–CH_3)–S–CH_2–CH_2–SC_2H_5  (3) | b.p. 140° C/0.01 mm Hg | $n_D^{19} = 1.5595$ |
| $C_2H_5O$–P(=S)(–NH–CH_3)–S–CH_2–SC_2H_5  (2) | b.p. 110° C/0.1 mm Hg | $n_D^{18.5} = 1.5675$ |
| $C_2H_5O$–P(=S)(–NH–iC_3H_7)–S–CH_2–SC_2H_5  (5) | b.p. 130° C/0.01 mm Hg | $n_D^{21.5} = 1.5460$ |
| $C_2H_5O$–P(=S)(–NH–iC_3H_7)–SCH_3 | m.p. 36° C | |

-continued

| Constitution | Physical properties | |
|---|---|---|
| (13) $C_2H_5O$, $S$ / $P$—$SC_2H_5$ / $iC_3H_7$—$NH$ | b.p. 95° C/0.01 mm Hg | $n_D^{21.5} = 1.5196$ |
| (14) $C_2H_5O$, $S$ / $P$—$SC_3H_7i$ / $iC_3H_7$—$NH$ | b.p. 92° C/0.01 mm Hg | $n_D^{24} = 1.5121$ |
| (15) $C_2H_5O$, $S$ / $P$—$S$—$CH_2$—$CH_2$—$Cl$ / $iC_3H_7$—$NH$ | b.p. 140° C/2.5 mm Hg | $n_D^{14} = 1.5374$ |
| (10) $C_2H_5O$, $S$ / $P$—$S$—$CH_2$—$CH$=$CH_2$ / $CH_3$—$NH$ | b.p. 105° C/0.01 mm Hg | $n_D^{20} = 1.5473$ |
| (16) $C_2H_5O$, $S$ / $P$—$S$—$CH_2$—$CH$=$CH_2$ / $iC_3H_7$—$NH$ | b.p. 96° C/0.01 mm Hg | $n_D^{20.5} = 1.5278$ |
| (17) $C_2H_5O$, $S$ / $P$—$S$—$CH_2$—$C$≡$CH$ / $CH_3$—$NH$ | b.p. 130° C/1 mm Hg | $n_D^{21.5} = 1.5553$ |
| (12) $C_2H_5O$, $S$ / $P$—$S$—$CH_2$—$C$≡$CH$ / $iC_3H_7$—$NH$ | b.p. 130° C/0.5 mm Hg | $n_D^{19} = 1.5378$ |
| (11) $C_2H_5O$, $S$ / $P$—$S$—$CH_2$—$CH_2$—$CH_2$—$CH_3$ / $CH_3$—$NH$ | b.p. 120° C/0.01 mm Hg | $n_D^{21.5} = 1.5238$ |
| (18) $C_2H_5O$, $S$ / $P$—$S$—$CH_2$—$CH_2$—$CH_2$—$CH_3$ / $iC_3H_7$—$NH$ | b.p. 110° C/0.01 mm Hg | $n_D^{21} = 1.5126$ |
| (19) $C_2H_5O$, $S$ / $P$—$S$—$CH_2$—(phenyl) / $CH_3$—$NH$ | b.p. 175° C/0.1 mm Hg | $n_D^{22} = 1.5893$ |
| (20) $C_2H_5O$, $S$ / $P$—$S$—$CH_2$—(phenyl) / $iC_3H_7$—$NH$ | b.p. 123° C/0.01 mm Hg | $n_D^{23} = 1.5672$ |
| (21) $C_2H_5O$, $S$ / $P$—$S$—$CH_2$—$S$—(phenyl)—$Cl$ / $CH_3$—$NH$ | | $n_D^{19} = 1.6297$ |
| (22) $C_2H_5O$, $S$ / $P$—$S$—$CH_2$—$S$—(phenyl)—$Cl$ / $iC_3H_7$—$NH$ | | $n_D^{23} = 1.5969$ |
| (23) $C_2H_5O$, $S$ / $P$—$S$—$CH_2$—$S$—(naphthyl) / $CH_3$—$NH$ | | $n_D^{23.5} = 1.6767$ |

(24)

| Constitution | Physical properties |
|---|---|
| 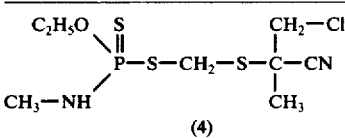 (4) | $n_D^{23} = 1.5668$ |
| 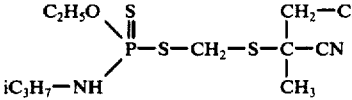 (6) | $n_D^{26.5} = 1.5492$ |
| 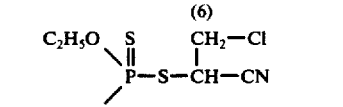 (25) | $n_D^{23} = 1.5333$ |
| 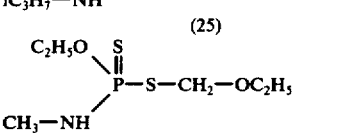 (26) | $n_D^{25} = 1.4331$ |
| 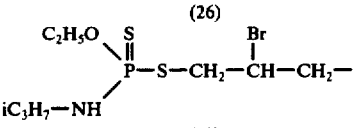 (27) | $n_D^{22} = 1.5674$ |
| 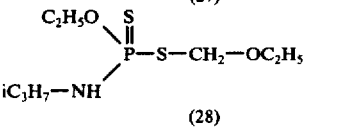 (28) | b.p. 89° C/0.01 mm Hg $\quad n_D^{24} = 1.5140$ |
| 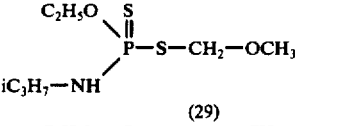 (29) | b.p. 72° C/0.01 mm Hg $\quad n_D^{24} = 1.5199$ |
| 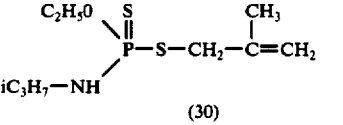 (30) | b.p. 99° C/0.05 mm Hg $\quad n_D^{22} = 1.5222$ |
| 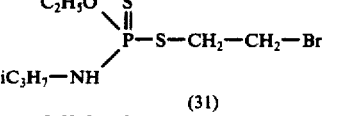 (31) | $n_D^{22} = 1.5439$ |
| 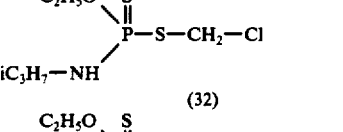 (32) | b.p. 85° C/0.01 mm Hg $\quad n_D^{23} = 1.5331$ |
| 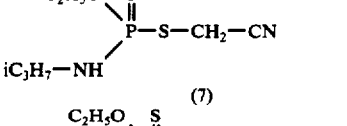 (7) | b.p. 102° C/0.01 mm Hg $\quad n_D^{24.5} = 1.5313$ |
| 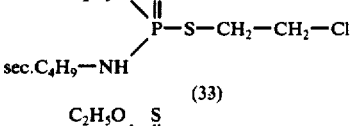 (33) | $n_D^{21} = 1.5301$ |
| 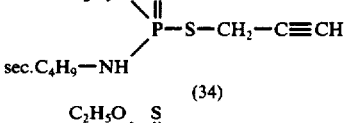 (34) | $n_D^{17.5} = 1.5350$ |
| 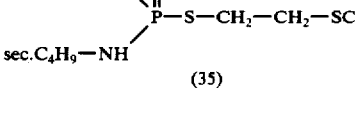 (35) | $n_D^{18} = 1.5394$ |

-continued

| Constitution | Physical properties |
|---|---|
| (36) C₂H₅O, S; P(=S)–S–CH₂–C≡CH; CH₂=CH–CH₂–NH | $n_D^{17.5} = 1.5542$ |
| (37) C₂H₅O, S; P(=S)–S–CH₂–CH₂–Cl; CH₂=CH–CH₂–NH | $n_D^{21} = 1.5475$ |
| (8) C₂H₅O, S; P(=S)–S–CH₂–CH₂–SC₂H₅; CH₂=CH–CH₂–NH | $n_D^{18} = 1.5544$ |
| (38) CH₃O–CH₂–CH₂–O, S; P(=S)–S–CH₂–CH₂–SC₂H₅; iC₃H₇–NH | $n_D^{17.5} = 1.5390$ |
| (39) CH₃O–CH₂–CH₂–O, S; P(=S)–S–CH₂–CH₂–Cl; iC₃H₇–NH | $n_D^{21} = 1.5312$ |
| (40) CH₃O–CH₂–CH₂–O, S; P(=S)–S–CH₂–C≡CH; iC₃H₇–NH | $n_D^{21} = 1.5352$ |
| (41) Cl₃C–CH₂–O, S; P(=S)–S–CH₂–C≡CH; iC₃H₇–NH | $n_D^{24} = 1.5483$ |
| (9) Cl₃C–CH₂–O, S; P(=S)–S–CH₂–CH₂–Cl; iC₃H₇–NH | $n_D^{23} = 1.5477$ |
| (42) Cl₃C–CH₂–O, S; P(=S)–S–CH₂–CH₂–SC₂H₅; iC₃H₇–NH | $n_D^{23} = 1.5497$ |
| (43) C₂H₅O, S; P(=S)–S–CH₂–CH₂–S–C₂H₅; CH₃S–CH₂–CH₂–NH | $n_D^{25} = 1.5683$ |
| (44) C₂H₅O, S; P(=S)–S–CH₂–S–C₂H₅; CH₃–S–CH₂–CH₂–NH | $n_D^{21} = 1.5745$ |
| (45) C₂H₅O, S; P(=S)–S–CH₂–CH=CH₂; CH₃S–CH₂–CH₂–NH | $n_D^{21} = 1.5634$ |
| (46) C₂H₅O, S; P(=S)–S–CH₂–C≡CH; CH₃–S–CH₂–CH₂–NH | $n_D^{21} = 1.5719$ |
| (47) C₂H₅O, S; P(=S)–S–C₂H₅; CH₃S–CH₂–CH₂–NH | $n_D^{25} = 1.5530$ |

-continued

| Constitution | Physical properties |
|---|---|
| (48) $C_2H_5O$, $iC_3H_7$-NH, P=S, S-CH$_2$-C=CH-Br, Br | $n_D^{20} = 1.5793$ |
| (49) $C_2H_5O$, $iC_3H_7$-NH, P=S, S-CH$_2$-CH$_2$-CH$_3$ | $n_D^{21} = 1.5143$ |
| (50) $C_2H_5O$, $iC_3H_7$-NH, P=S, S-CH$_2$-CH-CH$_2$-Cl, Cl | $n_D^{26} = 1.5440$ |
| (51) $C_2H_5O$, $iC_3H_7$-NH, P=S, S-CH$_2$-CH=CH-CH$_3$ | $n_D^{27.5} = 1.5251$ |
| (52) $C_2H_5O$, $iC_3H_7$-NH, P=S, S-CH$_2$-CH-CH-CH$_3$, Cl Cl | $n_D^{23.5} = 1.5399$ |
| (53) $C_2H_5O$, $iC_3H_7$-NH, P=S, S-CH$_2$-CH=C-CH$_3$, Cl | $n_D^{25} = 1.5363$ |
| (54) $C_2H_5O$, $iC_3H_7$-NH, P=S, S-CH, CH$_2$-Cl, C=CH$_2$, Cl | $n_D^{24.5} = 1.5490$ |
| (55) CH$_2$=CH-CH$_2$-O, $iC_3H_7$-NH, P=S, S-CH$_2$-CH$_2$-Cl | $n_D^{23.5} = 1.5375$ |
| (56) CH$_2$=CH-CH$_2$-O, $iC_3H_7$-NH, P=S, S-CH$_2$-C≡CH | $n_D^{23.5} = 1.5412$ |
| (57) CH$_2$=CH-CH$_2$-O, $iC_3H_7$-NH, P=S, S-CH$_2$-CH$_2$-S-C$_2$H$_5$ | $n_D^{23.5} = 1.5437$ |
| (58) $C_2H_5O$, $iC_3H_7$-NH, P=S, S-CH$_2$-C=CH, Cl Cl | $n_D^{24} = 1.5522$ |
| (59) $C_2H_5O$, C$_6$H$_{11}$-NH, P=S, S-CH$_2$-CH$_2$-S-C$_2$H$_5$ | $n_D^{23} = 1.5538$ |
| (60) $C_2H_5O$, C$_6$H$_{11}$-NH, P=S, S-CH$_2$-C≡CH | $n_D^{23} = 1.5512$ |

-continued

| Constitution | Physical properties |
|---|---|
| 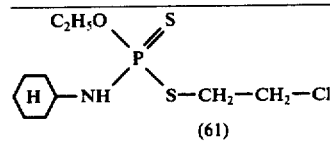 (61) | $n_D^{23} = 1.5477$ |
| 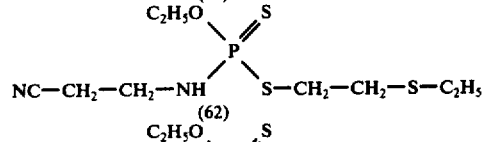 (62) | $n_D^{27.5} = 1.5551$ |
| 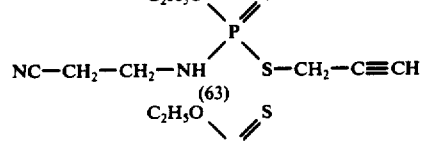 (63) | $n_D^{27.5} = 1.5546$ |
| 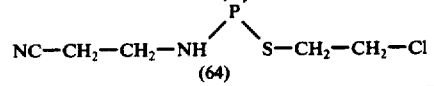 (64) | $n_D^{27.5} = 1.5512$ |

It will be appreciated that the instant specification and examples are set forth by way of illustration and not limitation, and that various modifications and changes may be made without departing from the spirit and scope of the present invention.

What is claimed is:

1. A thionophosphoric acid ester amide of the formula

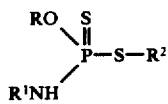

in which
- R and R¹ each is an alkyl or alkenyl radical with up to 6 carbon atoms, optionally substituted with at least one halo, phenyl, cyano, alkoxy, alkylmercapto, phenylmercapto or naphthylmercapto radical, the mercapto radicals being optionally chloro-or cyano-substituted, and
- R² is an alkynyl radical with up to 6 carbon atoms optionally substituted with at least one halo, phenyl, alkoxy, alkylmercapto, phenylmercapto or naphthylmercapto radical, the mercapto radicals being optionally chloro-substituted, or an alkyl or alkenyl radical with up to 6 carbon atoms substituted with a cyano radical or substituted with a cyano-substituted alkylmercapto, chloro substituted alkylmercaptor, phenylmercapto or naphthylmercapto radical.

2. A thionothiolphosphoric acid ester amide of the formula

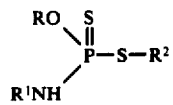

in which
- R is an alkyl or alkenyl radical with up to 4 carbon atoms optionally substituted with at least one halo or lower alkoxy radical,
- R¹ is cyanoalkyl with up to 4 carbon atoms, and
- R² is an alkyl radical with up to 4 carbon atoms substituted with at least one halo or lower alkymercapto radical.

3. A thionothiolphosphoric acid ester amide of the formula

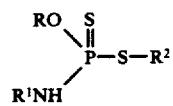

in which
- R is an alkyl or alkenyl radical with up to 4 carbon atoms optionally substituted with at least one halo or lower alkoxy radical,
- R¹ is lower alkylmercapto-lower alkyl, and
- R² is alkyl, alkenyl or alkynyl with up to 4 carbon atoms optionally substituted with at least one halo, phenyl, cyano, lower alkoxy, lower alkylmercapto, phenylmercapto or naphthylmercapto radical, the mercapto radicals being optionally chloro- or cyano-substituted.

4. A thionothiolphosphoric acid ester amide of the formula

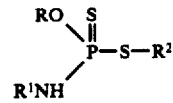

in which
- R is an alkyl radical with up to 4 carbon atoms and substituted with a lower alkoxy radical.
- R¹ is alkyl or alkenyl with up to 4 carbon atoms, and
- R² is alkyl with up to 4 carbon atoms optionally substituted by halo or lower alkylmercapto-lower alkyl.

5. A compound according to claim 1, in which R and R¹ each is an alkyl or alkenyl radical with up to 4 carbon atoms, and R² is propargyl.

6. A compound according to claim 5, wherein such compound is O-ethyl-S-propargyl-N-isopropyl-thionothiolphosphoric acid ester amide of the formula

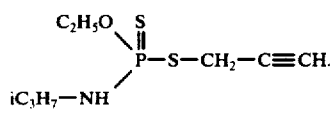

7. A compound according to claim 5, wherein such compound is O-ethyl-S-propargyl-N-methyl-thionothiolphosphoric acid ester amide of the formula

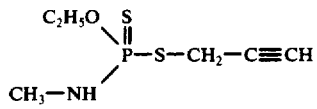

8. A compound according to claim 1 in which R and R¹ each is an alkyl or alkenyl radical with up to 4 carbon atoms, and R² is an alkyl or akenyl radical of up to 4 carbon atoms (carrying at least one) substituted with a cyano radical, or a cyano-substituted lower alkylmercapto, chloro-substituted lower alkylmercapto, phenylmercapto or naphthylmercapto radical.

9. A compound according to claim 8, wherein such compound is O-ethyl-S-(1-chloromethyl-1-cyano-ethyl-mercaptomethyl)-N-methyl-thionothiolphosphoric acid ester amide of the formula

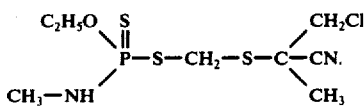

10. A compound according to claim 8, wherein such compound is O-ethyl-S-(1-chloromethyl-1-cyano-ethyl-mercaptomethyl)-N-isopropyl-thionthiolphosphoric acid ester amide of the formula

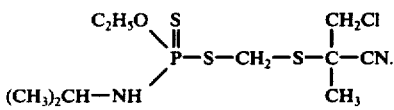

11. A compound according to claim 8, wherein such compound is O-ethyl-S-cyanomethyl-N-isopropyl-thionothiolphosphoric acid ester amide of the formula

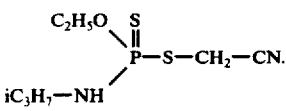

12. A composition for combating a pest selected from the group consisting of insects, acarids, fungi and namatodes which comprises an amount effectiveto kill such pest of a thionothiolphosphoric acid ester amide of the formula

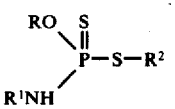

in which
R and R¹ each is an alkyl or alkenyl radical with up to 6 carbon atoms, optionally substituted with at least one halo, phenyl, cyano, alkoxy, alkylmercapto, phenylmercapto or naphthylmercapto radical, the mercapto radicals being optionally chloro-or cyano-substituted, and R² is an alkynyl radical with up to 6 carbon atoms optionally substituted with at least one halo, phenyl, alkoxy, alkylmercapto, phenylmercapto or naphthylmercapto radical, the mercapto radicals being optionally chloro-substituted, or an alkyl or alkenyl radical with up to 6 carbon atoms substituted with a cyano radical or substituted with a cyano-substituted alkylmercapto, chloro substituted alkylmercapto, phenylmercapto or naphthylmercapto radical.

13. The composition of claim 12 in which R and R¹ each is an alkyl or alkenyl radical with up to 4 carbon atoms, and R² is propargyl.

14. A composition according to claim 12, wherein such compound is

O-ethyl-S-propargyl-N-methyl-thionothiolphosphoric acid ester amide,

O-ethyl-S-(1-chloromethyl-1-cyano-ethylmercaptomethyl)-N-isopropyl-thionothiolphorphoric acid ester amide, O-ethyl-S-cyanomethyl-N-isopropyl-thionothiolphosphoric acid ester amide, or O-ethyl-S-(1-chloromethyl-1-cyano-ethylmercaptomethyl)-N-methyl-thionothiolphosphoric acid ester amide.

15. The method of combating a pest selected from the group consisting of insects, acarids, fungi and nematodes which comprises applying to said pest or a habitat thereof an amount effective to kill such pest of a thionothiolphosphoric acid ester amide of the formula

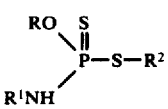

in which
R and R¹ each is an alkyl or alkenyl radical with up to 6 carbon atoms, optionally substituted with at least one halo, phenyl, cyano, alkoxy, alkylmercapto, phenylmercapto or naphthylmercapto radical, the mercapto radicals being optionally chloro-or cyano-substituted, and R² is an alkynyl radical with up to 6 carbon atoms optionally substituted with at least one halo, phenyl, alkoxy, alkylmercapto, phenylmercapto or naphthylmercapto radical, the mercapto radicals being optionally chloro-substituted, or an alkyl or akenyl radical with up to 6 carbon atoms substituted with a cyano radical or substituted with a cyano-substituted alkylmercapto, chloro substituted alkylmercapto, phenylmercapto or naphthylmercapto radical.

* * * * *